(12) United States Patent
Timmermans et al.

(10) Patent No.: US 7,578,618 B2
(45) Date of Patent: Aug. 25, 2009

(54) X-RAY EXAMINATION DEVICE

(75) Inventors: Roger Anton Marie Timmermans, Eindhoven (NL); Raymond Wilhelmus Louis Lafarre, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/065,624

(22) PCT Filed: Sep. 8, 2006

(86) PCT No.: PCT/IB2006/053179

§ 371 (c)(1),
(2), (4) Date: Mar. 4, 2008

(87) PCT Pub. No.: WO2007/029209

PCT Pub. Date: Mar. 15, 2007

(65) Prior Publication Data

US 2008/0226036 A1    Sep. 18, 2008

(30) Foreign Application Priority Data

Sep. 9, 2005    (EP) .................................. 05108305

(51) Int. Cl.
H05G 1/02    (2006.01)
(52) U.S. Cl. .................................................... 378/197
(58) Field of Classification Search .......... 378/196–198
See application file for complete search history.

(56) References Cited

U.S. PATENT DOCUMENTS

| | | | |
|---|---|---|---|
| 4,209,706 A | | 6/1980 | Nunan et al. |
| 4,894,855 A | | 1/1990 | Kresse |
| 4,922,512 A | * | 5/1990 | Lajus et al. ................. 378/197 |
| 4,987,585 A | * | 1/1991 | Kidd et al. .................. 378/197 |
| 5,038,371 A | * | 8/1991 | Janssen et al. .............. 378/197 |
| 5,521,957 A | * | 5/1996 | Hansen ....................... 378/198 |
| 5,583,909 A | * | 12/1996 | Hanover ...................... 378/197 |

(Continued)

FOREIGN PATENT DOCUMENTS

DE    19839825 C1    1/1998

(Continued)

OTHER PUBLICATIONS

Hagmann et al: "A Haptic Guidance Tool for CT-Directed Percutaneous Interventions"; Proceedings of the 26th Annual International Conference of the IEEE Engineering in Medicine and Biology Society, 2004, vol. 1, pp. 2746-2749.

(Continued)

*Primary Examiner*—Edward J Glick
*Assistant Examiner*—Thomas R Artman

(57) ABSTRACT

The invention concerns an X-ray examination device (10) comprising an X-ray source (20), an X-ray detector (18) and a segmented carrier, where the X-ray source and the X-ray detector are rotatable together around an isocentre (32). The segmented carrier includes a main arm (12) on which the X-ray source and X-ray detector are mounted and at least one first auxiliary arm (22) to which the main arm is mounted. The first auxiliary arm is rotatable around a first rotational axis (30) through the isocentre. The present invention provides an improved X-ray examination device that allows the provision of a greater freedom of selection of inspection angles regarding a patient

8 Claims, 4 Drawing Sheets

U.S. PATENT DOCUMENTS

| | | | |
|---|---|---|---|
| 6,264,364 B1 * | 7/2001 | Pflaum et al. | 378/196 |
| 6,309,102 B1 * | 10/2001 | Stenfors | 378/197 |
| 6,382,833 B2 * | 5/2002 | Leandersson et al. | 378/197 |
| 6,435,715 B1 | 8/2002 | Betz et al. | |
| 6,461,039 B1 * | 10/2002 | Klotz et al. | 378/197 |
| 6,742,929 B2 * | 6/2004 | Horbaschek | 378/197 |
| 2002/0118793 A1 | 8/2002 | Horbaschek et al. | |
| 2004/0008820 A1 | 1/2004 | Schmitt | |

FOREIGN PATENT DOCUMENTS

| | | |
|---|---|---|
| DE | 19839825 C1 | 10/1999 |
| EP | 0717954 A2 | 6/1996 |
| EP | 1090585 A1 | 4/2001 |

OTHER PUBLICATIONS

E. Hagmann et al., "A Haptic Guidance Tool for CT-Directed Percutaneous Interventions", Proceedings of 26th Annual International Conference of the IEE Engineering in Medicine and Biology Society, Sep. 2004, EMBC 2004, vol. 1, pp. 2746-2749.

* cited by examiner

X-RAY EXAMINATION DEVICE

TECHNICAL FIELD

The present invention is generally related to the field of medical inspection devices. The present invention is more particularly directed towards an X-ray examination device comprising a main arm having an X-ray source and an X-ray detector.

BACKGROUND OF THE INVENTION

In the field of X-ray examination devices, there are continuous efforts being made for designing the devices to provide as wide angles of inspection of the body as possible. This does also have to be combined with an ergonomically well functioning device for the staff handling it. This means that the medical staff should be able to easily access the patient in order to for instance perform operations while at the same time not having to change the position of the patient when inspections of the patient are to be made from various angles. This is quite a challenge.

In doing this there have been a number of solutions proposed for X-ray examination devices. One such solution is the so called C-arc solution, where an X-ray source is provided at one end of a C-shaped arm or arc and an X-ray detector is provided at the other end of the C-shaped arm facing the X-ray source. The C-shaped arm can then be turned round an isocentre using a guiding system. This C-shaped system allows large rotation angles but is however normally limited regarding patient coverage, i.e. it is normally not possible to inspect the whole body of the patient without moving the patient or the system. Such guiding systems are furthermore often complex, bulky and may limit access to the patient.

Another system is the so called G-based system, where a G-shaped arm or arc is used instead. This arc allows better patient coverage but is however more limited regarding supported inspection angles. Also this device uses a big guiding system.

US 2004/0008820 describes the use of an X-ray examination device having a main C-shaped arm provided with a radiation receiver and a radiation source, where these units face each other. The main arm can be turned around an isocentre. The C-shaped arm is connected to a device moving mechanism. The device moving mechanism is connected to the ceiling, wall or floor of a room and provides two axes of rotation for enabling movement of the whole device.

However it would be of interest to provide an alternative X-ray examination device that enables an even greater freedom of selection of inspection angles regarding a patient.

SUMMARY OF THE INVENTION

One object of the present invention is therefore to provide an improved X-ray examination device, and particularly one which provides a greater freedom of selection of inspection angles regarding a patient or the patient accessibility.

According to the present invention, this object is achieved by an X-ray examination device comprising:
- an X-ray source,
- an X-ray detector,
- the X-ray source and the X-ray detector being rotatable together around an isocentre,
- a segmented carrier including
  - a main arm on which the X-ray source and X-ray detector are mounted,
  - at least one first auxiliary arm to which the main arm is mounted, and
- wherein the first auxiliary arm is rotatable around a first rotational axis through the isocentre.

The present invention has a number of advantages. It has large rotation freedom combined with good patient coverage, without limiting the accessibility to the patient. The device is furthermore very general in nature and can be used for a multitude of applications. It is thus very suitable for a large range of examination types. The device according to the invention is furthermore very flexible, which makes it possible to use for several different types of medical examination applications. It is also compact and simple in that a limited number of moving parts are provided. Another advantage is that if the present invention is used for 3D-reconstruction, larger data sets can be obtained because of the wider angular range According to claim 2 the main arm is rotatably mounted to the first auxiliary arm by a first mechanical coupler that forms a second rotational axis through the isocentre around which the main arm can rotate and the first auxiliary arm is connected to a second mechanical coupler defining said first rotational axis, the first and second axis forming a first angle between them. This enables the movement of the main arm such that it does not unnecessarily block medical staff and the patient being examined. Since mechanical couplers that define rotational axes are provided for rotation, there is no need for large curved guidings that are normally expensive, complicated and bulky compared with such mechanical couplers in order to obtain similar stiffness and accuracy. Because of this it is furthermore easier to provide cabling for the device.

According to claim 3 there is a second auxiliary arm joined to the first auxiliary arm via said second mechanical coupler and provided with a third mechanical coupler for being fastened to another element and according to claim 4 the third mechanical coupler provides a third rotational axis through the isocentre around which the second auxiliary arm may be rotated, wherein the first and second rotational axes form a second angle between them. This even further enhances the flexibility and enlarges the number of inspection angles that can be provided.

According to claim 5 the first and second angles are equal. This feature allows the device to become more compact in its construction.

According to claim 6 the third mechanical coupler is movably connected to the second auxiliary arm. This feature has the advantage of allowing flexibility in the positioning of the device.

According to claim 7 each auxiliary arm has a shape that complements at least between mechanical couplers the shape of each arm it is connected to and according to claim 8 the main arm includes at least one curved section between a first position defined by the first mechanical coupler and a second position that may cross the first rotational axis between the second mechanical coupler and the isocentre. These features have the advantage of avoiding disturbing the rotation of other arms and providing a compact design.

According to, claim 9 the first angle is 90 degrees or below.

According to claim 10 the first angle is between 50 and 70 degrees. This feature allows the device to be turned with great liberty for achieving different angles towards the isocentre, while at the same time allowing easy access to the whole body of the patient.

According to one advantageous version of the present invention the first and second auxiliary arms are equally long.

According to another advantageous version of the present invention the third mechanical coupler is connected to the ceiling, wall or floor of a room. This feature allows the device to be placed such that it does not unnecessarily disturb medical staff.

According to yet another advantageous version of the present invention each mechanical coupler that provides a rotational axis is in the form of a bearing or bearing-like element.

The basic idea of the invention is to provide an X-ray examination device having an X-ray source and an X-ray detector, where the X-ray source and the X-ray detector are rotatable together around an isocentre. The device further comprises a segmented carrier including a main arm on which the X-ray source and X-ray detector are mounted and at least one first auxiliary arm to which the main arm is mounted. The first auxiliary arm is rotatable around a first rotational axis through the isocentre. In this way the present invention provides an improved X-ray examination device, and particularly one which allows the provision of a greater freedom of selection of inspection angles regarding a patient.

The above mentioned and other aspects of the invention will be apparent from and elucidated with reference to the embodiments described hereinafter.

BRIEF DESCRIPTION OF THE DRAWINGS

The present invention will be further described in relation to the accompanying drawings, in which.

DETAILED DESCRIPTION OF THE INVENTION

The present invention is generally directed towards an X-ray examination device for inspecting the body of a patient. In the following a device will be described having a C-shaped main arm or arc. It should however be realized that the present invention can be used with other configurations of the main arm, like for instance a G-shaped arm. In fact the present invention provides a great freedom in the way arms may be shaped.

Figure 1:
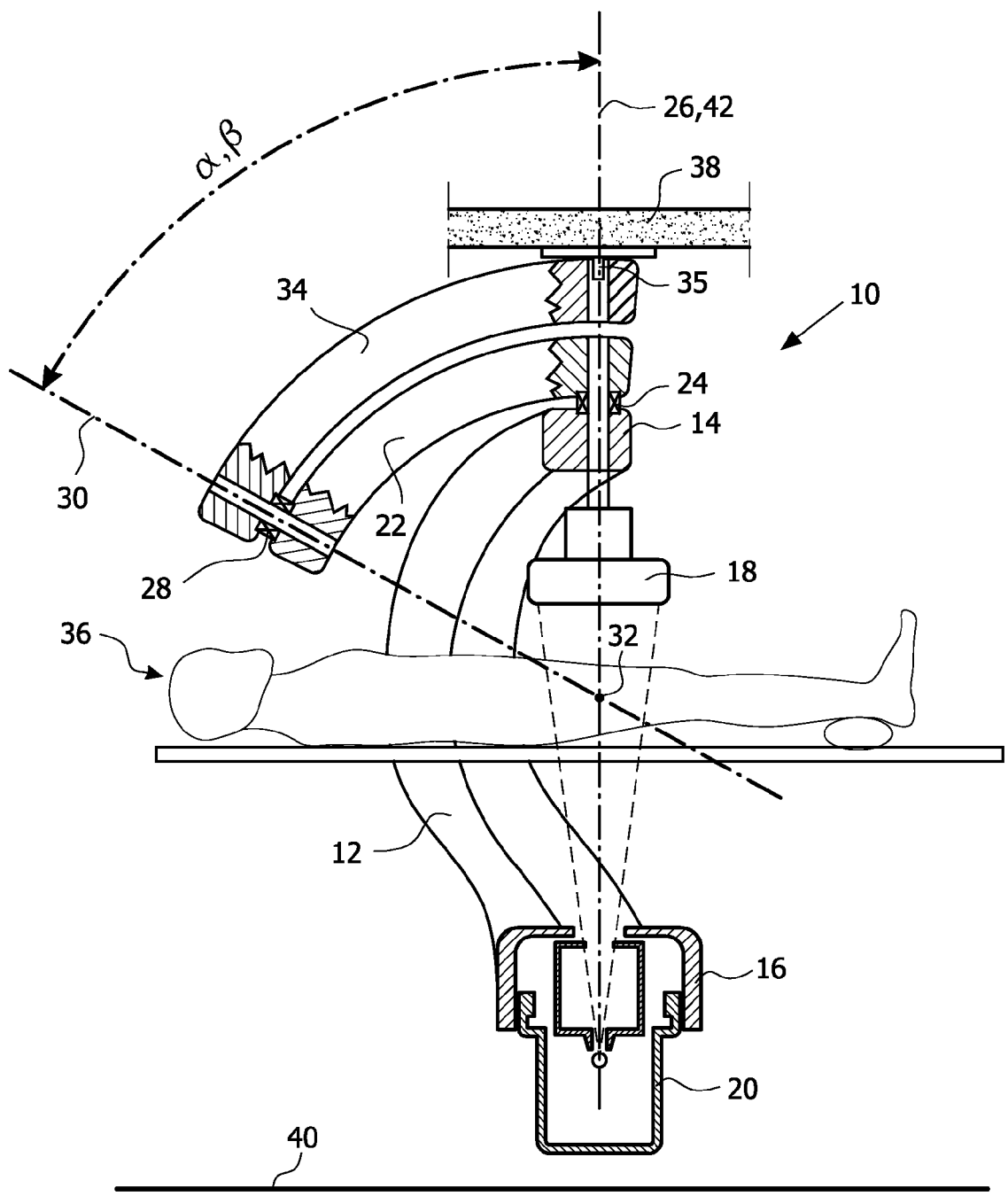
FIG. 1 shows a sectional view of an X-ray examination device according to the present invention in a first exemplifying position.

FIG. 1 shows a sectional view of an embodiment of the X-ray examination device 10 according to the present invention in a first exemplifying position. The device 10 according to the present invention comprises a segmented carrier including a main arm 12 and a number of auxiliary arms 22 and 34, which are here two. The main arm 12 is here shaped as a C or as half a circle and has two opposite ends, a first end 14, where an X-ray detector 18 is provided, and a second end 16, where an X-ray source 20 is provided. In FIG. 1, the main arm 12 stretches obliquely into the plane of the paper. The X-ray source 20 and the X-ray detector 18 face each other such that the X-ray source 20 emits X-ray radiation in a cone-shaped beam towards the X-ray detector 18, where the beam encircles a line 26 between the X-ray source 20 and the X-ray detector 18. This radiation then passes through the body of a patient 36 and is received by the X-ray detector 18. X-ray images are then formed out of these detected X-rays. The X-ray images are then displayed in an examination room or can be viewed on a radiologist's workstation, where they can be commented on and then forwarded to a physician, such that the physician can make an analysis of the results of the radiation of the body.

The main arm 12 is at the first end 14 connected to a first auxiliary arm 22 via a first mechanical coupler in the form of a first bearing 24 or bearing-like element. The first auxiliary arm 22 is furthermore connected to a second auxiliary arm 34 via a second mechanical coupler in the form of a second bearing 28 or bearing-like element, which second bearing 28 defines a first rotational axis 30 around which the first auxiliary arm 22 may be turned. In the same way the first bearing 24 provides a second rotational axis 26, where the first bearing 24 provides this axis between the X-ray source 20 and the X-ray detector 18. The second bearing 28 is distanced from the first bearing 24 on the first auxiliary arm such that the two axes of rotation 26 and 30 form a first angle α between them. This relationship between the axes furthermore makes them pass through an isocentre 32, which is defined on a suitable distance on the second rotational axis 26 between the X-ray source and X-ray detector. This point is furthermore preferably chosen so that it is on a height that is suitable for medical staff to work with the device and a patient being inspected. The first auxiliary arm 22 is in this embodiment also curved and has a shape complementary to the shape of the main arm 12 such that it does not disturb the rotational freedom of the main arm 12. The bearings 24 and 28 may be provided anywhere on the first auxiliary arm 22, but are preferably provided at two opposite ends of the first auxiliary arm 22 in order to provide as compact a design as possible.

The second auxiliary arm 34 is in this embodiment connected to a wall, floor or ceiling of a room and here to the ceiling 38 of a room via a third mechanical coupler in the form of a third bearing 35 or bearing-like element. This third bearing 35 forms a third axis of rotation 42, which in FIG. 1 coincides with the second rotational axis 26, and around which the second auxiliary arm 34 may be turned. The third bearing 35 is distanced from the second bearing 28 on the second auxiliary arm 34 in such a way that the first 30 and third 42 axis of rotation form a second angle β between them. This angle β is in this embodiment equal to the first angle α, but it should be realized that it does not have to be so in other embodiments of the present invention. Also the third axis 42 passes through the isocentre 32. The second auxiliary arm 34 is in this embodiment also curved and has a shape complementary to the shape of the first auxiliary arm 22 such that it does not disturb the rotational freedom of the first auxiliary arm 22. The shape is thus here in the form of a section of a circle. The bearings 28 and 35 may be provided anywhere on the second auxiliary arm 34, but are preferably provided at two opposite ends of the second auxiliary arm in order to provide as compact a design as possible of the device.

In a preferred embodiment the whole main arm 12 is curved between the two ends 14 and 16. It is however sufficient if it includes at least one curved section between the first bearing 24 and a position that crosses the first rotational axis 30 between the second bearing 28 and the isocentre 32, when the main arm 12 is rotated.

The device is, as was mentioned above, fastened to the ceiling 38 of a room and is thus suspended above ground 40, which allows a flexible way of changing the positions of the device for allowing inspection of a patient 36 from a wide variety of angles. This also allows it to be less disturbing for the medical staff. In this way the third axis 42 is stationary in the embodiment, while the first 30 and second axes 26 may be moved for achieving the various inspection angles.

The first angle α is in the present embodiment approximately 60 degrees as is the second angle β. This allows the device according to the present invention to be turned with great liberty for achieving different angles towards the isocentre. This allows the coverage of the isocentre by approximately 240 degrees, while at the same time allowing easy accessibility to the patient.

All rotational axes stretch through the corresponding arm that is to be rotated and through the isocentre as a contrast to customary X-ray examination devices using main arms, where three stacked and fixed orthogonal rotational axes are provided.

In FIG. 1 the two auxiliary arms 22 and 34 are provided aligned with each other, where the second auxiliary arm 34 is provided on top of the first auxiliary arm 22 so that the second and third rotational axes coincide. This is a nominal position of the device, which is the starting point for inspection of a patient. When the auxiliary arms are provided in this way, all parts of a patient 36 are easily accessible. Radiation is here emitted from straight under the patient and upwards.

Figure 2:
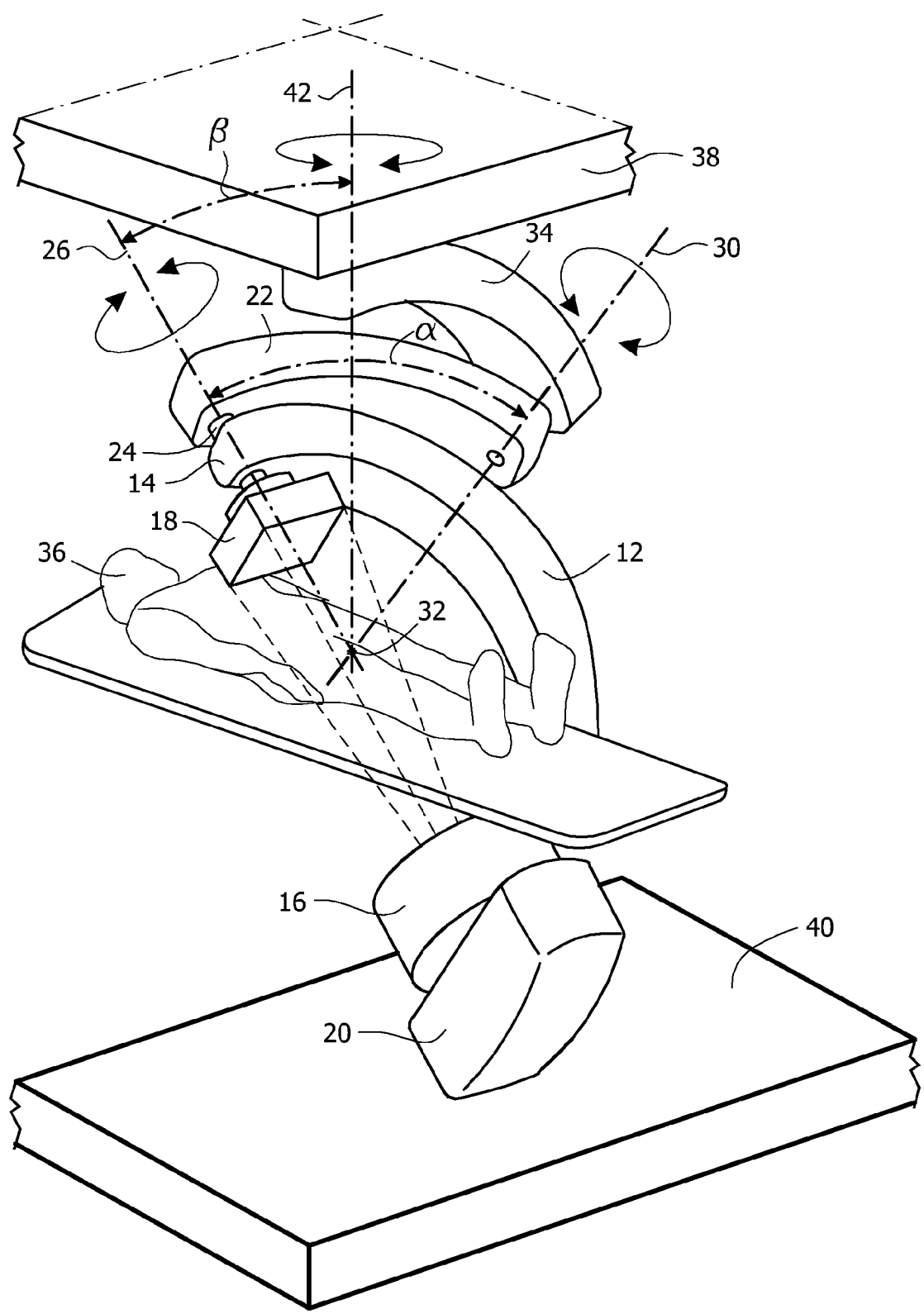
FIG. 2 shows a perspective view of the device in a second exemplifying position.
Figure 3:
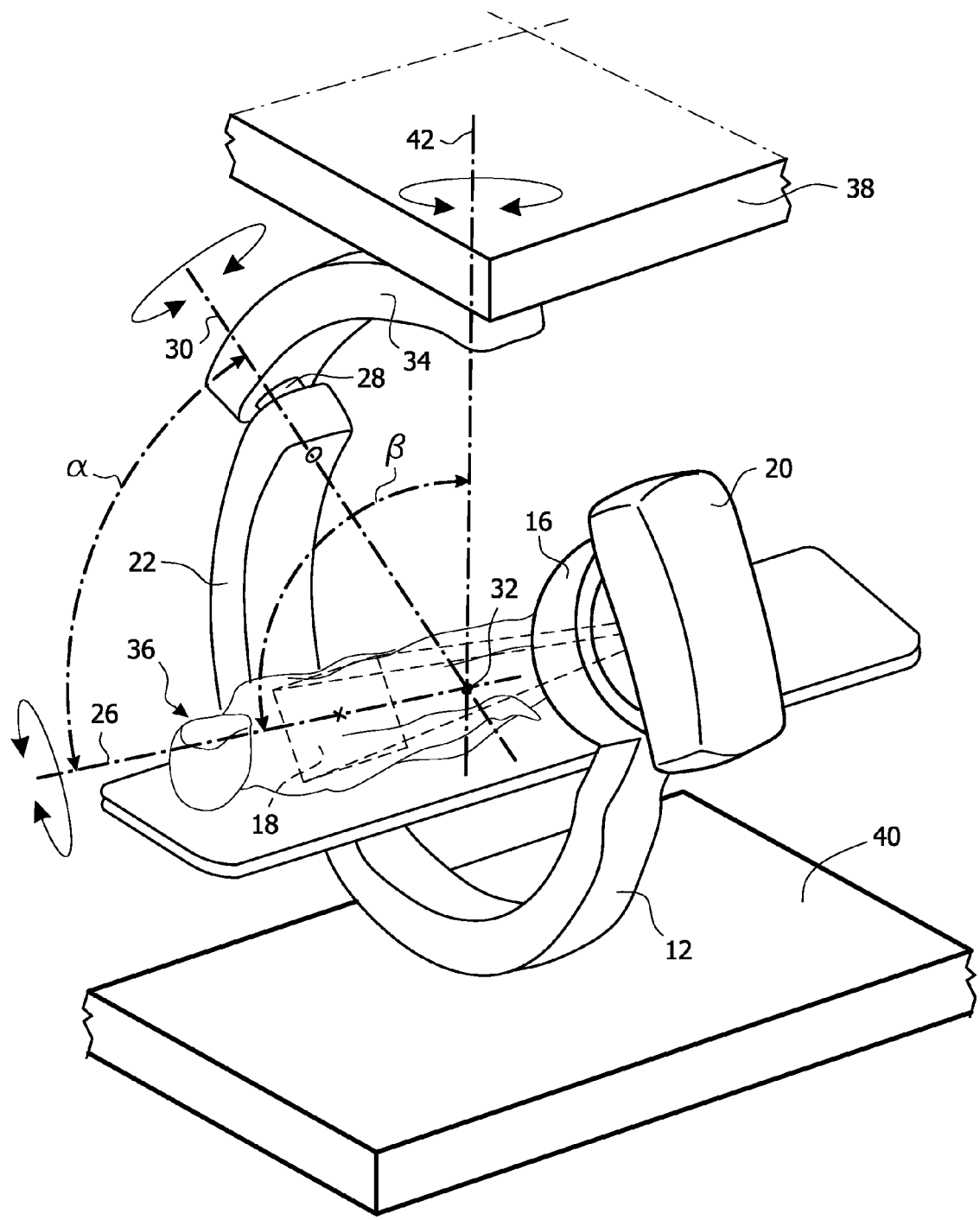
FIG. 3 shows a perspective view of the device in a third exemplifying position.
Figure 4:
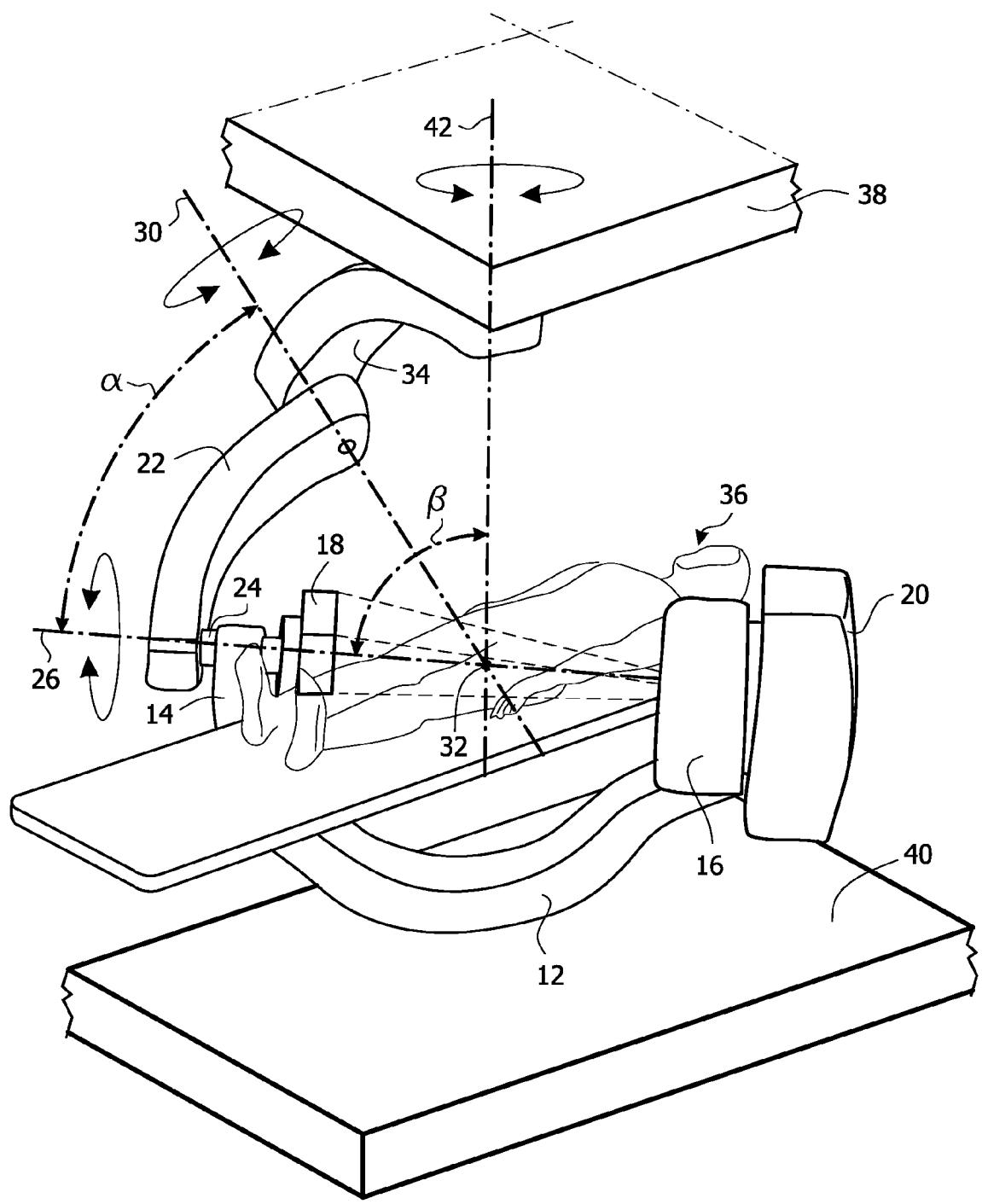
FIG. 4 shows a perspective view of the device in a fourth exemplifying position.

FIG. 2-4 show perspective views of the device according to the described embodiment as the different axes have been turned for providing a different inspection angle. In FIG. 2 the first 30, the second 26 and the third 42 rotational axes are shown together with the first and second angles α and β. Here the first axis 30 has been moved, by rotating the second auxiliary arm 34, in relation to the third axis 42 so that it now is provided on the left side of the third axis 42. This has positioned the first rotational axis 30 so that it meets the isocentre 32 obliquely from above and sideways towards the patient body 36. The first auxiliary arm 22 has here been turned to the left of the first axis 30 so that the second axis 26 meets the isocentre 32 obliquely from above along the length of the patient 36. This provides the possibility to emit radiation in a direction obliquely from below along the length direction of the patient onto the isocentre.

FIG. 3 shows another position of the device of the described embodiment. Here the second auxiliary arm 34 is turned left round the third axis 42, while the first auxiliary arm 22 has also been turned left round the first rotational axis 30. The main arm 12 has furthermore been turned such that the device forms part of a circle encircling the waist of the patient. This allows the possibility to emit radiation obliquely from above through the waist of the patient body.

FIG. 4 shows how the third auxiliary arm 34 has been turned approximately 180 degrees round the third axis 42 compared with FIG. 3, while the first auxiliary arm 22 has been angled somewhat upwards around the first axis 30 so that the second rotational axis 26 is essentially provided in the same plane as the patient. This allows the possibility to emit radiation straight from the side onto the patient.

The different positions shown in FIG. 1-4 are all exemplifying for showing the great possibilities of varying the inspection angle according to the present invention. It should be realized that countless others exist.

The present invention has a number of advantages. It has large rotation freedom combined with good patient coverage, without limiting the accessibility to the patient. The device is furthermore very general in nature and can be used for a multitude of applications. It is thus very suitable for a large range of examination types. With the device according to the described embodiment it is thus possible to have great variations regarding inspection angles, where the provision of the first auxiliary arm and first rotational axis provide a good number of possible angles. The provision of the third axis and the second auxiliary arm even further enhances the flexibility of inspection angles. The provision of the second rotational axis enables the movement of the main arm such that it does not unnecessarily block medical staff and the patient being examined. The provision of the first and second angles of 60 degrees furthermore has the advantage of allowing easy access to the whole body of the patient, and then in particular the head, as can be seen in FIG. 1, while still providing a great variety of inspection angles. The device according to the invention is furthermore very flexible, which makes it possible to use for several different types of medical examination applications. It is also compact and simple in that a limited number of moving parts are provided. Since bearings are provided for rotation, there is no need for large curved guidings that are normally expensive, complicated and bulky compared with bearings in order to obtain similar stiffness and accuracy. Because of this it is furthermore easier to provide cabling for the device.

There are a number of variations that can be made to the present invention. First of all it is possible that the main arm is fixedly attached to the first auxiliary arm. This would still allow a great number of inspection angles. It is furthermore possible that the second auxiliary arm is omitted. In this case the second bearing could be directly attached to a wall. This would limit the number of inspection angles, but provide a simpler construction of the device. When the second auxiliary arm is provided, it can furthermore be fixedly attached to the ceiling instead, which limits the number of angles somewhat but provides a device that has a simpler construction. It is furthermore possible to provide even further auxiliary arms in the segmented carrier and that may be stacked above each other in the same way as the first and second auxiliary arm are stacked above each other in FIG. 1. The additional auxiliary arms would then each be connected with another auxiliary arm using bearings providing rotational axes in the same way as the first and second auxiliary arm. The shape of the main arm and the auxiliary arms can be varied in numerous ways. The only thing that has to be considered though are that the X-ray source and X-ray detector face each other, that the moving parts do not disturb the rotation of other parts and that the rotational axes all meet at the isocentre. The first and second angles need furthermore not be the same but can be different in size. However if they are the same the device becomes less bulky. They can both be below 90 degrees, where a higher angle provides a greater freedom in selection of inspection angles. For instance, if both the first and the second angle were 90 degrees, it is possible to provide inspection angles covering 360 degrees, whereas a smaller first and second angle provides better access to and less disturbance of the patient. However for best accessibility without having to provide arcs having too large a radius, it is preferred to provide an angle between 50 and 70 degrees. The mechanical couplers need furthermore not be bearings or bearing-like elements. It is also possible to provide mechanical couplers using a hinging technique, such that one of the elements joined by a mechanical coupler is provided with a tap or rod intended to mate with a corresponding recess of the other element. It is furthermore possible that both elements are provided with cavities or holes arranged to mate with and encircle a tap or rod.

The second auxiliary arm was here connected to the ceiling. It could just as well be connected to another wall, like the floor or a side wall of a room. It is furthermore possible that the whole X-ray examination device is movable through the second auxiliary arm being movably connected to a positioning device, for example a linear slide, comprising two bars interconnected by a bearing providing a rotational axis, where one of the bars would be connected to the second auxiliary arm and the other bar could be connected to a wall via a further bearing providing yet another rotational axis. It should be realized that the positions of the X-ray source and X-ray detector could be the opposite of the one shown in the drawings. The arms need furthermore not be curved although this is preferred since then smooth rotation without disturbances is much easier to implement. The main arm may for example be shaped as a G-arc or as a part of an ellipse. The lower part of the main arm need not be curved, but only the upper part provided adjacent the first and second auxiliary arms. The length of the auxiliary arms can be varied.

Although the present invention has been described in connection with specific embodiments, it is not intended to be limited to the specific form set forth herein. Rather, the scope of the present invention is limited only by the accompanying claims. In the claims, the term comprising does not exclude the presence of other elements. Additionally although individual features may be included in different claims, these may possibly be advantageously combined and the inclusion in different claims does not imply that a combination of features is not feasible and/or advantageous. In addition singular references do not exclude a plurality. Thus references to "a", "an", "first", "second" etc. do not preclude a plurality. Reference signs in the claims are provided merely as a clarifying example and shall not be construed as limiting the scope of the claims in any way.

The invention claimed is:

1. An X-ray examination device comprising:
   an X-ray source,
   an X-ray detector,
   a segmented carrier comprising
      a main arm on which the X-ray source and X-ray detector are mounted,
      a first auxiliary arm having a first end and a second end, wherein the first auxiliary arm is rotatable around a first rotational axis passing through the first end of the auxiliary arm and through the isocentre, and wherein one end of the main arm is rotatably mounted to the second end of the first auxiliary arm by a first mechanical coupler that forms a second rotational axis through the isocentre around which the main arm can rotate, the first auxiliary arm being connected to a second mechanical coupler defining the first rotational axis, the first and second axes forming a first angle ($\alpha$) between them, and
      a second auxiliary arm joined to the first auxiliary arm via said second mechanical coupler providing said first rotational axis, said second auxiliary arm being provided with a third mechanical coupler for being fastened to another element.

2. X-ray examination device according to claim 1, wherein the third mechanical coupler provides a third rotational axis through the isocentre around which the second auxiliary arm may be rotated, wherein the first and third rotational axes form a second angle ($\beta$) between them.

3. X-ray examination device according to claim 2, wherein the first and second angles are equal.

4. X-ray examination device according to claim 1, wherein the third mechanical coupler is movably connected to the second auxiliary arm.

5. X-ray examination device according to claims 1, wherein each auxiliary arm has a shape that complements at least between mechanical couplers the shape of each arm it is connected to.

6. X-ray examination device according to claim 5, wherein the main arm includes at least one curved section between a first position defined by the first mechanical coupler and a second position that may cross the first rotational axis between the second mechanical coupler and the isocentre.

7. X-ray examination device according to claims 1, wherein the first angle ($\alpha$) is 90 degrees or below.

8. X-ray examination device according to claim 7, wherein the first angle ($\alpha$) is between 50 and 70 degrees.

* * * * *